US011415516B2

(12) United States Patent
Sood et al.

(10) Patent No.: US 11,415,516 B2
(45) Date of Patent: Aug. 16, 2022

(54) METHOD FOR REDUCTION OF AUTOFLUORESCENCE FROM BIOLOGICAL SAMPLES

(71) Applicant: Leica Microsystems CMS GmbH, Wetzlar (DE)

(72) Inventors: Anup Sood, Clifton Park, NY (US); Arunkumar Natarajan, Niskayuna, NY (US); Dmitry Dylov, Niskayuna, NY (US); Lakshmi Sireesha Kaanumalle, Niskayuna, NY (US); Elizabeth Mary McDonough, Niskayuna, NY (US)

(73) Assignee: LEICA MICROSYSTEMS CMS GMBH, Wetzlar (DE)

(*) Notice: Subject to any disclaimer, the term of this patent is extended or adjusted under 35 U.S.C. 154(b) by 253 days.

(21) Appl. No.: 15/299,085

(22) Filed: Oct. 20, 2016

(65) Prior Publication Data
US 2017/0122872 A1 May 4, 2017

Related U.S. Application Data

(60) Provisional application No. 62/247,400, filed on Oct. 28, 2015.

(51) Int. Cl.
*G01N 21/64* (2006.01)
*G01N 33/574* (2006.01)
*G01N 33/483* (2006.01)

(52) U.S. Cl.
CPC ..... *G01N 21/6458* (2013.01); *G01N 33/4833* (2013.01); *G01N 33/57407* (2013.01); *G01N 21/6428* (2013.01); *G01N 2021/6439* (2013.01); *G01N 2333/70503* (2013.01); *G01N 2333/91215* (2013.01)

(58) Field of Classification Search
CPC ....... G01N 2021/6439; G01N 21/6428; G01N 21/6458; G01N 2333/70503; G01N 2333/91215; G01N 33/4833; G01N 33/57407

See application file for complete search history.

(56) References Cited

U.S. PATENT DOCUMENTS

| 7,629,125 | B2 | 12/2009 | Sood et al. | |
| 9,176,032 | B2* | 11/2015 | Sood | G01N 33/582 |
| 2013/0137119 | A1* | 5/2013 | Wilkes | G01N 21/6486 435/7.37 |
| 2013/0178392 | A1* | 7/2013 | Sood | G01N 1/30 506/9 |

OTHER PUBLICATIONS

Kumar et al., "Rapid and simple method of photobleaching to reduce background autofluorescence in lung tissue sections," Indian J. Biochem. Biophys., Feb. 2015, vol. 52, No. 1, pp. 107-110.*
Duong et al., "A multispectral LED array for the reduction of background autofluorescence in brain tissue," J. Neuroscience Methods, vol. 220, issue 1, Oct. 30, 2013, pp. 46-54.*
Chiang et al., "Design and demonstration of high efficiency antiglare LED luminaires for indoor lighting," Opt. Express, Feb. 9, 2015, vol. 23, No. 3, pp. A15-A26; first published Dec. 22, 2014.*
A printout "LED 470 nm" retrieved from https://www.google.com/search?source=hp&ei=SfDAW4v7ONKMggew2YzoBg&q=LED+470+nm&btnK=Google+Search&oq=LED+470+nm&gs_l=psy-ab.3..0i22i30i8.245712.261526..263487 ...0.0..0.60.457.10......0....1.. gws-wiz.......0j0i131j0i22i10i30.-A8XNkrQd7U on Oct. 12, 2018.*
Davis et al., "Characterizing and Diminishing Autofluorescence in Formalin-fixed Paraffin-embedded Human Respiratory Tissue," J. Histochem. Cytochem., 2014, vol. 62, No. 6, pp. 405-423.*
Karpishin, "Reducing Tissue Autofluorescence," Gen. Eng. Biotech. News, Mar. 1, 2018, vol. 38, No. 5, pp. 1-7.*

* cited by examiner

*Primary Examiner* — Galina M. Yakovleva
(74) *Attorney, Agent, or Firm* — Leydig, Voit & Mayer, Ltd.

(57) ABSTRACT

The invention discloses a method for reduction of autofluorescence in biological samples, comprising the steps of:
a) providing a biological microscopy sample;
b) irradiating the sample with visible light, wherein the visible light has a spectrum such that at least 50% of the light intensity emanates from a narrow wavelength interval within the visible range. The invention also discloses a method for autofluorescence reduction with triplet sensitizers irradiated with visible light.

33 Claims, 13 Drawing Sheets

| Intensity (% of peak intensity) | M385LP1 | M455L3 | M490L3 | M505L3 | M530L3 |
|---|---|---|---|---|---|
| 10% | 374 nm | 431 nm | 475 nm | 482 nm | 488 nm |
| 20% | 377 nm | 436 nm | 478 nm | 488 nm | 492 nm |
| 40% | 379 nm | 440 nm | 482 nm | 496 nm | 496 nm |
| 60% | 381 nm | 443 nm | 485 nm | 500 nm | 500 nm |
| 80% | 383 nm | 446 nm | 487 nm | 503 nm | 503 nm |
| 100% | 386 nm | 451 nm | 494 nm | 512 nm | 513 nm |
| 80% | 388 nm | 457 nm | 500 nm | 519 nm | 529 nm |
| 60% | 391 nm | 460 nm | 504 nm | 524 nm | 538 nm |
| 40% | 393 nm | 464 nm | 507 nm | 532 nm | 543 nm |
| 20% | 397 nm | 472 nm | 516 nm | 548 nm | 550 nm |
| 10% | 401 nm | 480 nm | 525 nm | 557 nm | 554 nm |

METHOD FOR REDUCTION OF AUTOFLUORESCENCE FROM BIOLOGICAL SAMPLES

TECHNICAL FIELD OF THE INVENTION

The invention relates generally to methods and systems for reducing inherent autofluorescence of biological materials in images of those biological materials and in particular to reduction of autofluorescence by photobleaching.

BACKGROUND OF THE INVENTION

Tissue auto-fluorescence (AF) is a fundamental problem in microscopy and surgical applications. It reduces the signal detection sensitivity, and in some cases may cause failure in the detection of fluorescent dye signals. Accurate detection of target-specific fluorescent dyes is critical for many microscopy applications, such as molecular pathology imaging, where quantitation of molecular pathways has significant implications such as predicting drug response, therapy planning, and population segmentation of cancer patients.

In recent years the development of numerous fluorescent dyes has made optical fluorescent microscopy the method of choice for biomedical research. Numerous studies have used fluorescent spectroscopy techniques to study the variations in tissue auto-fluorescence for diagnosis of colorectal, breast, lung, cervical, colon, gastrointestinal tract, and cancer. However, these methods require extensive modeling of tissue-specific auto-fluorescence (AF) spectra. This tedious modeling process, which may not always be sufficient, can be side stepped by using multiplexing techniques in which artificially introduced dyes or dyes are used to track specific histological features and/or molecular targets such as protein, DNA, RNA, carbohydrates, lipid, etc. Multiplexing involves acquiring images of different dyes with non-overlapping emission or excitation spectra through filter cubes that match the emission and excitation spectra of each dye. However, in such methods, the protein-specific fluorescence emitted by these dyes, upon appropriate external light excitation, is combined in unknown proportions with the inherent tissue autofluorescence (AF) signal, greatly reducing their efficacy. Thus separation and significant reduction of inherent tissue AF would greatly improve the accuracy of such methods.

Although various strategies for tissue AF reduction have been proposed and studied in the literature, such as, using liquid crystal tunable filters, fluorescence polarization, dual-wavelength differential fluorescence correction, confocal laser scanning microscopy and time-resolved fluorescence microscopy, many of these strategies make use of expensive multi-spectral imaging hardware, over the entire spectral range, followed by spectral un-mixing. Apart from hardware augmentation, there are also various chemical processes that can be used to reduce the effect of tissue AF.

Digitally acquired fluorescence microscope images can also be processed retrospectively using software methods, to separate tissue AF from the relevant dye fluorescence. Some of these methods rely on acquiring estimates of the pure AF signal and using them to reduce AF from images containing both dye and AF signals by a weighted subtraction. Others use statistical correlation techniques to correct for the additive AF signal. While these techniques are more cost effective than using multi-spectral imaging hardware, they may not be able to completely reduce the AF component from fluorescence microscopy images as the AF may be altered due to treatments used to generate the target-specific signal.

Accordingly, there is a need for further improved methods to decrease the AF intensity from microscopy samples.

SUMMARY OF THE INVENTION

One aspect of the invention is to provide a method for significant reduction of autofluorescence from biological samples, which method is rapid and easy to perform and does not damage the sample. This is achieved with the methods as defined in the claims.

One advantage is that the signal-to-noise ratio (S/N) is increased for the fluorescent signal in fluorescence microscopy. This applies particularly when the signals of interest are weak.

A further advantage is that a stable background signal can be achieved. This is generally desirable, but is particularly important in multiplexed imaging such as disclosed e.g. in U.S. Pat. No. 7,629,125, which is hereby incorporated by reference in its entirety, where several background images need to be acquired if the remaining AF intensity is not stable.

A yet further advantage is that antigen epitopes and nucleic acids in the sample are not blocked or damaged, which allows for reliable staining by immunolabeling or nucleic acid hybridization.

Another aspect of the invention is to provide an apparatus for simple and efficient reduction of autofluorescence from biological samples. This is achieved with an apparatus as defined in the claims.

Further suitable embodiments of the invention are described in the dependent claims.

DRAWINGS

Figure 4:
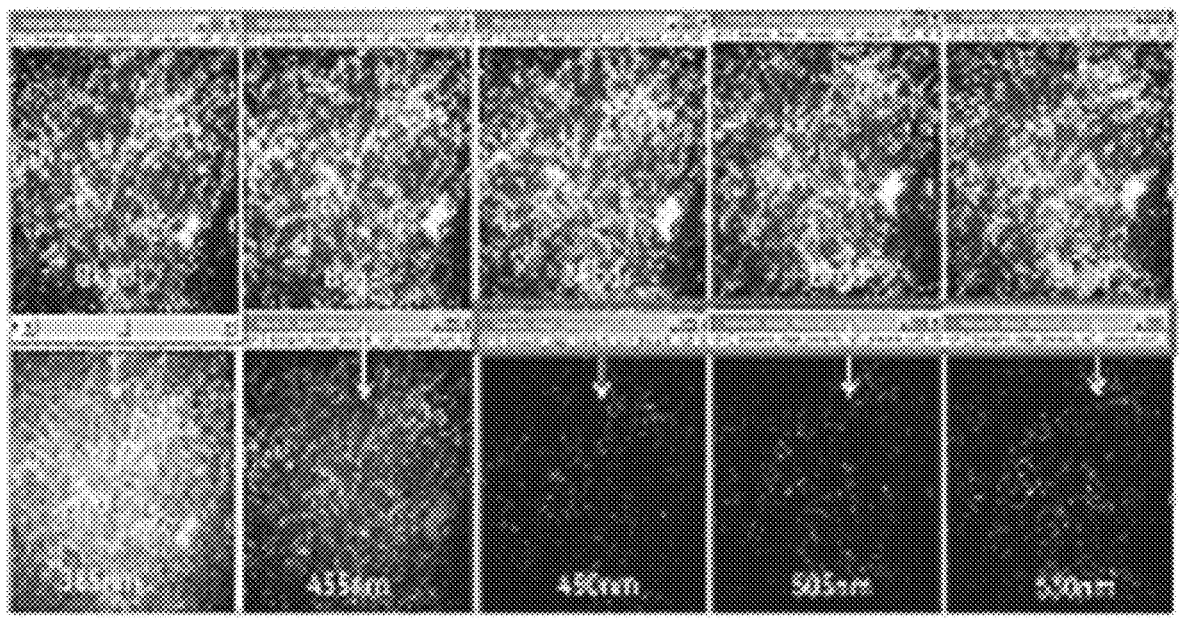

FIG. 4 shows autofluorescence reduction on Folio-Tcell Lymphoma tissue using 5 different LED wavelengths-385, 455, 505 (130 mW/cm$^2$) and 490 and 530 nm's using (60 mW/cm$^2$) for 30 minutes. 490, 505 and 530 nm LEDs result in more effective AF reduction than 455 nm LED which itself reduces AF. Bleaching with 385 nm LED on the other hand, shows an increase in AF.

Figure 5:
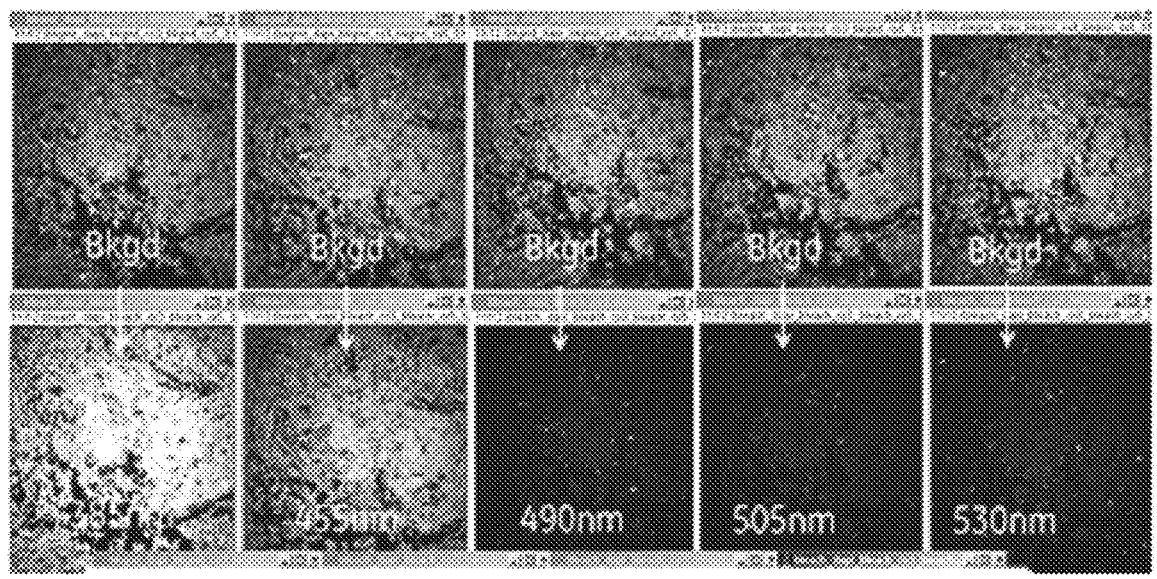

FIG. 5 shows autofluorescence reduction on Reactive lymph node tissue using 5 different LED wavelengths-385, 455, 505 (130 mW/cm$^2$) and 490 and 530 nm's using (60 mW/cm$^2$) for 30 minutes. 490, 505 and 530 nm LEDs result in significant AF reduction, whereas 385 and 455 nm LED exposure shows increase in AF.

Figure 6:
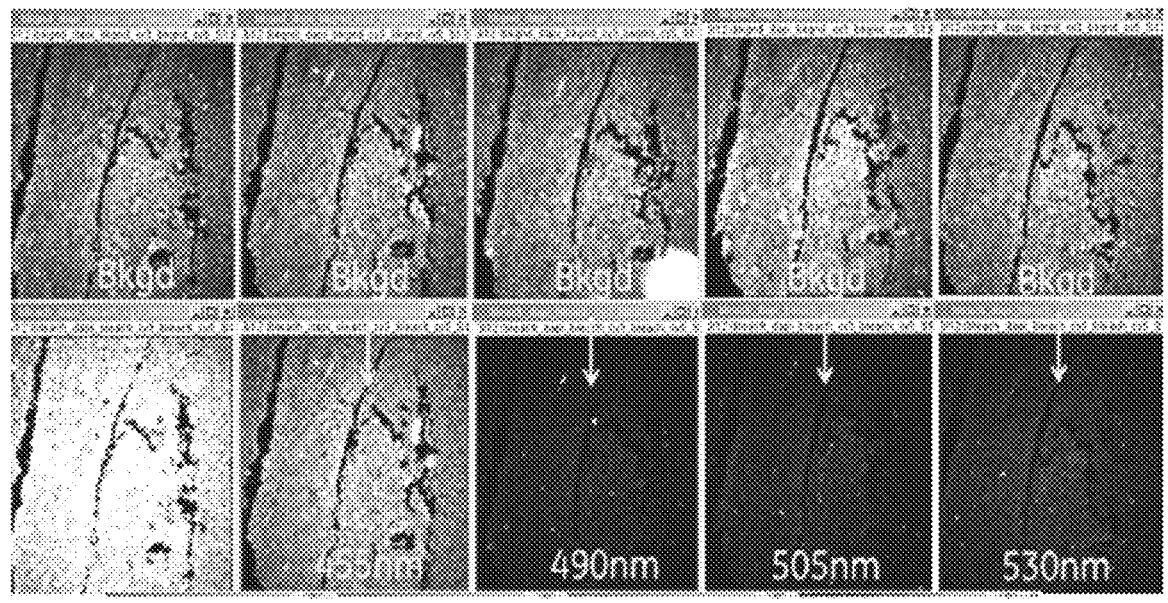

FIG. 6 shows autofluorescence reduction on Hodgkins lymphoma tissue using 5 different LED wavelengths-385, 455, 505 (130 mW/cm$^2$) and 490 and 530 nm's using (60 mW/cm$^2$) for 30 minutes. 490, 505 and 530 nm LEDs result in effective AF reduction, whereas 385 and 455 nm LED exposure shows increase in AF.

Figure 7:
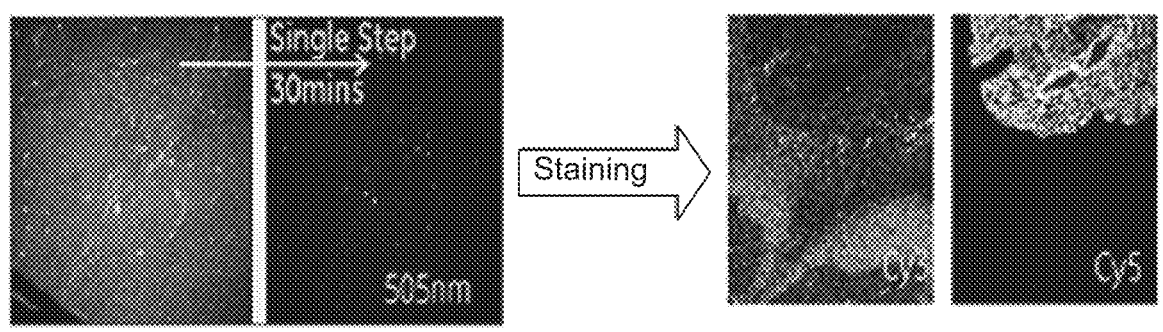

FIG. 7 shows Staining with CD79 (Cy3 channel) and PCK26 (Cy5 channel) after autofluorescence reduction using 505 nm LED.

Figure 8:
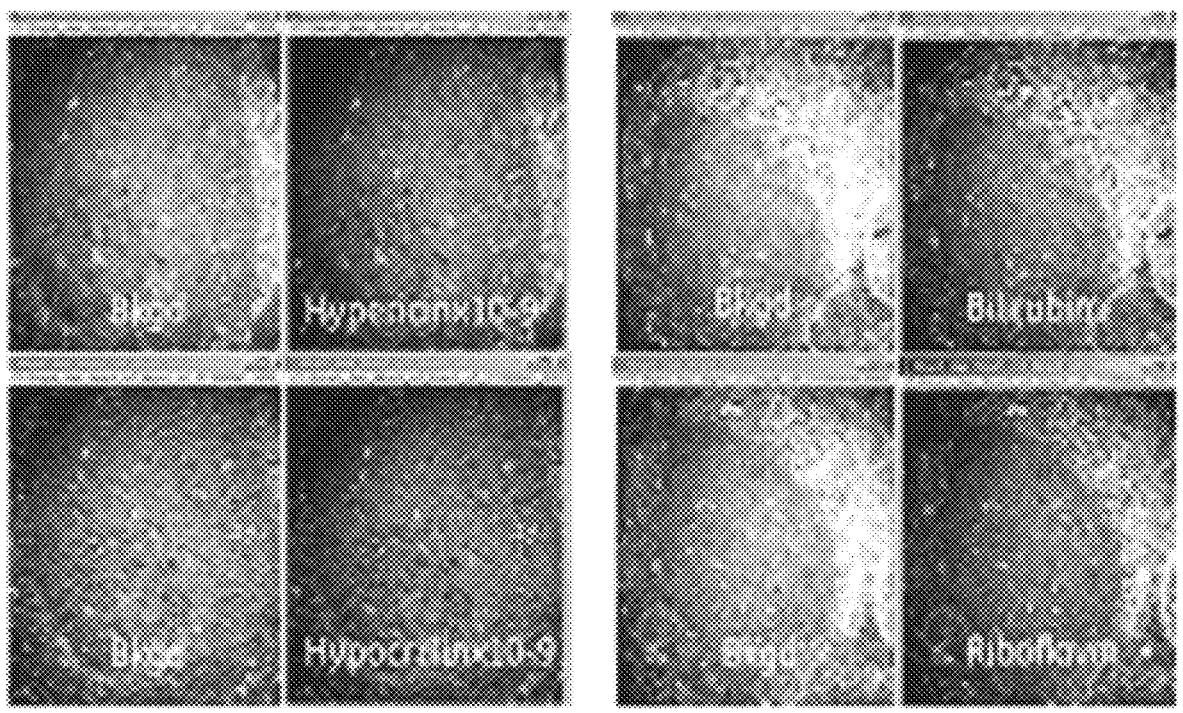

FIG. 8 shows autofluorescence reduction on Tonsil tissue Cy3-Channel (top left) Bkgd-native background and exposure to 10$^{-9}$M hypericin in PBS (top right) native background vs exposure to 10$^{-6}$M bilirubin in PBS, (bottom left)

Bkgd-native background and exposure to $10^{-9}$M hypocrellin and (bottom right) Bkgd-native background and exposure to $10^{-6}$M riboflavin. All the tissues are exposed to 20 minutes to visible light (420 nm rayonet bulbs, 5 mW/cm$^2$).

Figure 9:
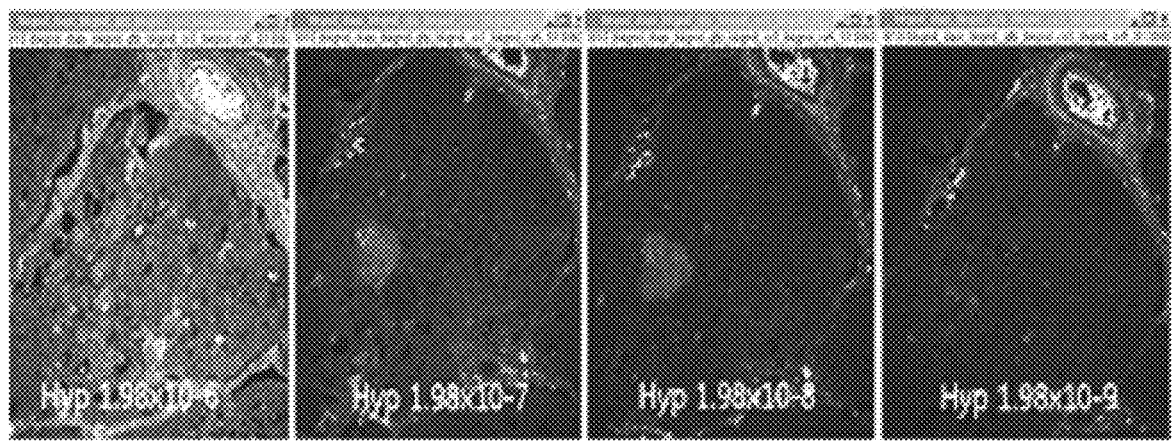

FIG. 9 shows autofluorescence reduction on Lung carcinoma tissue: Bkgd-native background and exposure to $10^{-9}$M hypericin in PBS and exposed to 20 minutes to 226 mW 549 nm LED.

Figure 10:
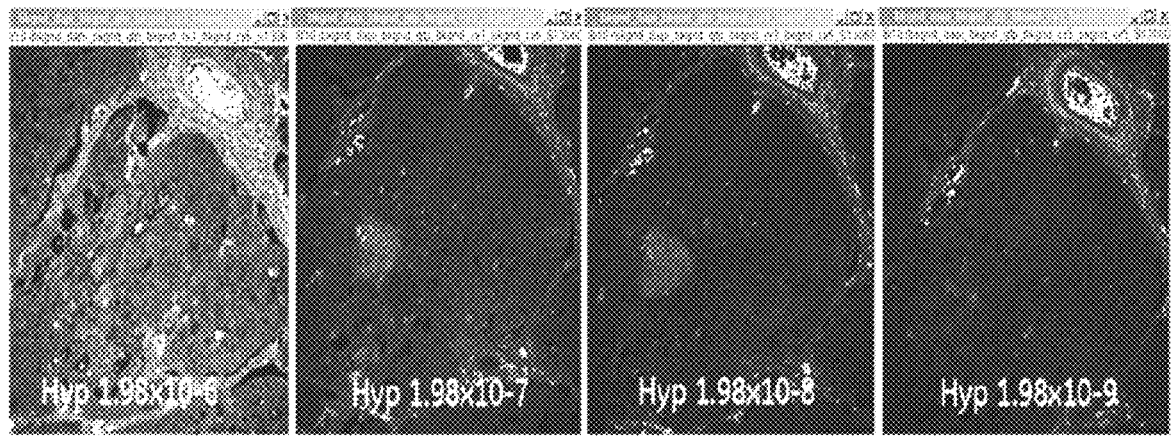

FIG. 10 shows autofluorescence reduction on Lung carcinoma tissue concentration dependence of hypericin in PBS while exposure (20 minutes) to 226 mW 549 nm LED. (bottom) Bkgd. The results suggest that hypericin lower than 10'M is efficient in AF reduction. At higher concentrations sensitizer aggregation or stacking reduces sensitization.

Figure 11:
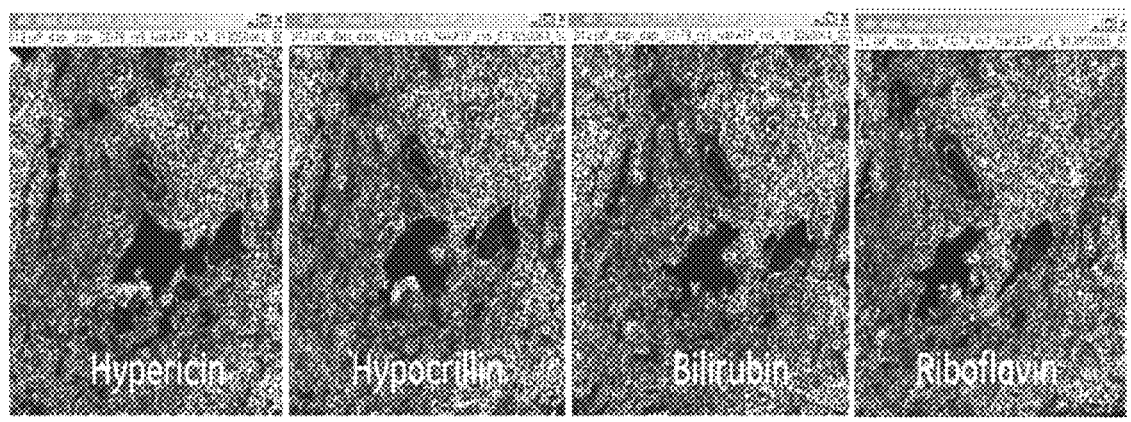

FIG. 11 shows staining with Cy5-NaKATPase on Diffuse B-Cell Lymphoma tissue after Autofluorescence reduction using treatment with triplet sensitizers Hypericin, Hypocrillin, Bilirubin and Riboflavin respectively. No effect is observed on subsequent staining indicating antigens are preserved.

Figure 12:
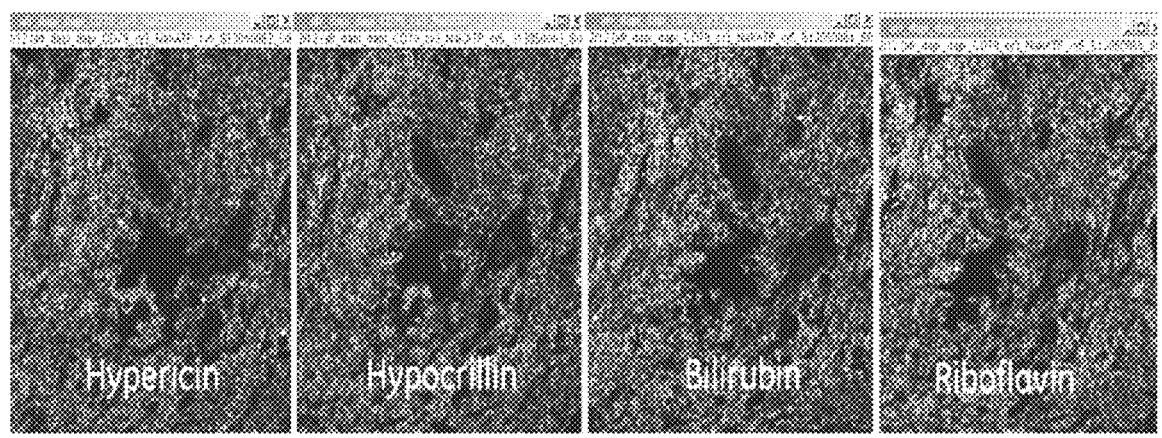

FIG. 12 shows staining with Cy3-CD79a on Diffuse B-Cell Lymphoma tissue after Autofluorescence reduction using treatment with triplet sensitizers Hypericin, Hypocrillin, Bilirubin and Riboflavin respectively.

FIG. 13 shows emission spectra of the LEDs used.

DEFINITIONS

To more clearly and concisely describe and point out the subject matter of the claimed invention, the following definitions are provided for specific terms that are used in the following description and the claims appended hereto.

The singular forms "a" "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. Accordingly, unless indicated to the contrary, the numerical parameters set forth in the following specification and attached claims are approximations that may vary depending upon the desired properties sought to be obtained by the embodiments of the present invention. At the very least each numerical parameter should at least be construed in light of the number of reported significant digits and by applying ordinary rounding techniques.

Any directional terms such as "top", "bottom", "above", "below" "up", "down" and "height" herein refer to the devices as they appear in the drawings. Joinder references (e.g., joined, attached, coupled, connected, and the like) are to be construed broadly and may include intermediate members between a connection of elements and relative movement between elements. As such, joinder references do not necessarily imply that two elements are connected directly and in fixed relation to each other. Further, various elements discussed with reference to the various embodiments may be interchanged to create entirely new embodiments coming within the scope of the present invention.

DETAILED DESCRIPTION OF EMBODIMENTS

In one aspect, the present invention discloses a method for reduction of autofluorescence in biological samples. The method comprises the steps a)-b) of:

a) Providing one or more biological microscopy sample. The sample(s) can e.g. be fixed on one or more microscope slide, which is convenient for subsequent analysis e.g. by fluorescence microscopy. Suitably the sample(s) may contain cells and it/they may comprise e.g. tissue material, material from body fluids, cultivated cells or any other source of animal, plant or microbial cells. The cells can e.g. be human cells, such as cells from patient samples. A typical example of a sample is a section of a formaldehyde fixed paraffin embedded (FFPE) tissue sample, which is commonly used for pathology imaging and analysis. FFPE tissue section samples can suitably be hydrated and deparaffinized before step b). They may also be contacted with an antigen retrieval solution before or after step b). Antigen retrieval solutions (commercially available) remove inactivating bonds introduced by the formaldehyde fixation so that antigens in the sample become capable of binding to antibody binders in subsequent staining procedures.

b) Irradiating the biological microscopy sample(s) with visible, or alternatively near infrared (NIR), light having a light intensity. The visible or NIR light has a spectrum such that a large fraction of the light intensity emanates from a narrow wavelength interval. Suitably, at least 50%, at least 70%, at least 80% or at least 90%, of the light intensity emanates from (is in) this narrow wavelength interval within the visible or NIR range. The visible range is typically about 390-700 nm, the NIR range typically about 700-2500 nm (in particular 700-1000 nm) and the width of the narrow wavelength interval is only a portion of this range and may e.g. be up to 80 nm or up to 70 nm, which is a comparatively small fraction of the visible/NIR range. The use of a narrow interval allows selection of wavelengths that reduce autofluorescence but which do not cause any damage to the sample(s). It also allows selection to avoid instability effects due to creation of new fluorophores by irradiation. More specifically, the wavelength interval may be 470-550 nm, such as 490-530 nm. The total light intensity in the irradiation step may be 5-300 mW/cm$^2$, such as 25-300 or 50-200 mW/cm$^2$ and the irradiation time may be 5-90 min, such as 10-60 min or 10-30 min. The irradiation may be carried out with one or more light emitting diodes (LED), which can have suitable spectral output for use in the method. When using more than one LED, the LEDs may all emit in the same narrow wavelength interval or LEDs with different narrow wavelength ranges may be combined. The LEDs may e.g. be mounted in a lightbox of suitable dimensions for irradiating one or more microscope slides. Suitably, the light intensity is spatially uniform over the sample(s). The coefficient of variation of the light intensity over the sample(s) may e.g. be less than 20%, such as less than 10% or less than 5%.

In some embodiments, the method further comprises, before step b), a step a') of contacting said sample with a solution comprising a triplet sensitizer. In this case, it can be advantageous to use a wavelength interval matching the absorption spectrum of the triplet sensitizer. The triplet sensitizer may e.g. be selected from the group consisting of riboflavin, bilirubin, hypericin, methylene blue and hypocrellin. In some cases the interval may e.g. be 515-585 nm, such as 530-570 nm. For further details about triplet sensitizers, see below.

In certain embodiments, the method further comprises a step c) of staining the sample with one or more fluorescent markers and imaging fluorescence from the sample. The fluorescent markers may e.g. be fluorescent histological stains, fluorophores conjugated to antibodies, fluorophores conjugated to nucleic acids or fluorophores conjugated to lipids, which can bind to specific structures, antigens, specific nucleic acid sequences or other targets in the sample. The sample may e.g. be stained repeatedly with different fluorescent markers, with a bleaching step between the staining steps, as outlined e.g. in U.S. Pat. No. 7,629,125, which is hereby incorporated by reference in its entirety. The method is particularly advantageous in this technique, as oxidation of endogenous fluorophores after each cycle can cause constant changing of the background signal. This necessitates reimaging of the background after each round for accurate mathematic reduction of autofluorescence. With the method of the invention, the endogenous autofluorescence is significantly reduced or at least stabilized at a very low level, eliminating the need for reimaging after each cycle.

In some embodiments, the method further comprises a step d) of analysing fluorescence images of the sample obtained in step c). The analysis may e.g. be carried out using an image analysis software on a computer and an outcome of the analysis may e.g. be a diagnosis or prognosis for a patient or an assessment of the effect of a pharmaceutical.

In a second aspect, the invention discloses a method for reduction of autofluorescence from biological samples. The method comprises the steps i)-iii) of:

Providing a biological microscopy sample. The sample can suitably be as discussed above.

Contacting the sample with a solution comprising a triplet sensitizer. A triplet sensitizer is a species capable of absorbing light, suitably visible light, undergoing vibrational relaxation and intersystem crossing to its triplet state, and then taking part in an energy transfer with a component in the sample. This sensitizer-mediated process leads to a reduction of autofluorescence in the sample. The triplet sensitizer is an aromatic species (molecule or ion), typically a conjugated aromatic ketone or imide. It may e.g. be selected from the group consisting of riboflavin, bilirubin, hypericin, methylene blue and hypocrellin A and B. These compounds contain conjugated aromatic structures and consequently have a high absorption of visible light.

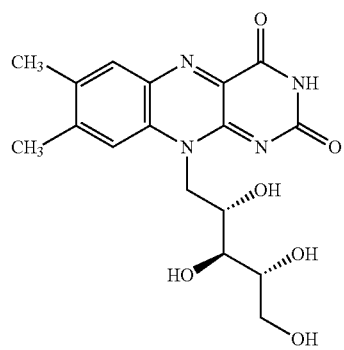

Riboflavin

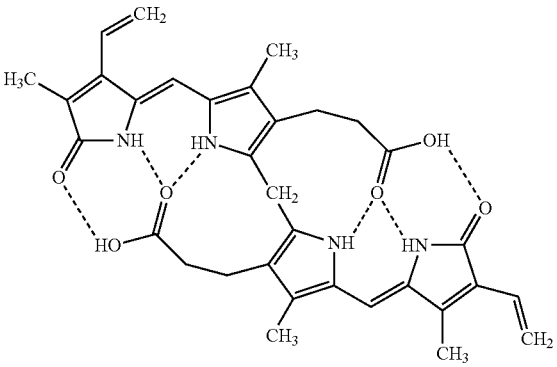

Bilirubin

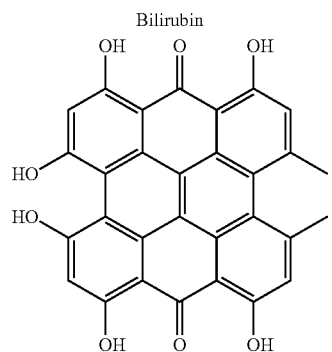

Hypericin

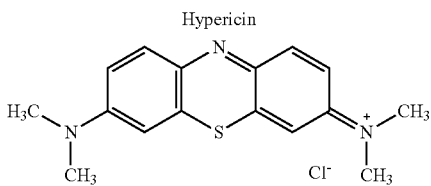

Methylene blue

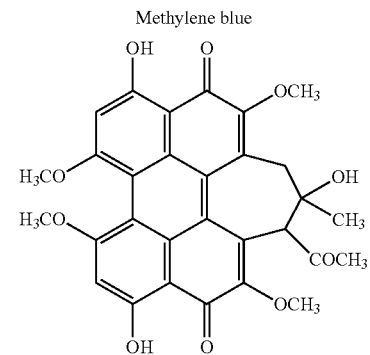

Hypocrellin A

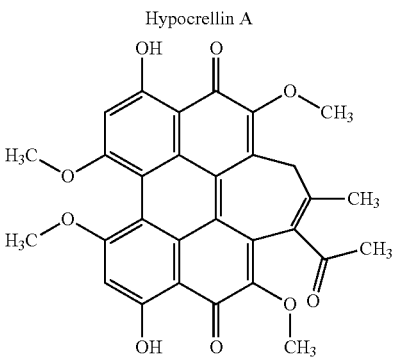

Hypocrellin B

TABLE 1

Approximate absorption maxima wavelengths in the visible range

| Compound | Wavelength (nm) |
|---|---|
| Riboflavin | 450 |
| Bilirubin | 480 |
| Hypericin | 540, 600 |
| Methylene blue | 680 |
| Hypocrellin A | 470 |
| Hypocrellin B | 470 |

The concentration of the triplet sensitizer in the solution may be $10^{-10}$ M to $10^{-5}$ M, such as $10^{-9}$ M to $10^{-6}$ M or $10^{-9}$ M to $10^{-7}$ M and the solution can e.g. be an aqueous solution such as an aqueous buffer. The contact time may be short, e.g. from 1 s, and the contacting may be carried out e.g. by dipping a microscope slide with the sample into the solution.

Irradiating the sample with visible or NIR light. The visible light may e.g. be provided by one or more light emitting diodes (LED) or fluorescent lamps, which may e.g. be mounted in a lightbox of suitable dimensions for irradiating one or more microscope slides. The total light intensity provided in the step may e.g. be 5-300 mW/cm², such as 50-200 mW/cm² and the irradiation time may e.g. be 5-90 min, such as 10-60 min or 10-30 min. The spectrum of the light may be matched to the absorption spectrum of the triplet sensitizer and as an example it can be about 420 nm for hypocrellin or riboflavin and about 550 nm for hypericin.

In certain embodiments, the method further comprises a step iv) of staining the sample with one or more fluorescent markers and imaging fluorescence from the sample. The fluorescent markers may e.g. be fluorescent histological stains, fluorophores conjugated to antibodies or antibody equivalents (e.g. antibody fragments, aptamers), fluorophores conjugated to nucleic acids (natural or modified) or fluorophores conjugated to lipids, which can bind to specific structures, antigens, specific nucleic acid sequences or other targets in the sample. The sample may e.g. be stained repeatedly with different fluorescent markers, with a bleaching step between the staining steps, as outlined e.g. in U.S. Pat. No. 7,629,125, which is hereby incorporated by reference in its entirety.

In some embodiments, the method further comprises a step v) of analysing fluorescence images of the sample obtained in step iv). The analysis may e.g. be carried out using an image analysis software on a computer and an outcome of the analysis may e.g. be a diagnosis or prognosis for a patient or an assessment of the effect of a pharmaceutical.

In a third aspect, the invention discloses a method for reduction of autofluorescence from biological samples, comprising the steps of:
I) providing a biological microscopy sample;
II) irradiating said sample with visible light from one or more light emitting diodes (LED), wherein said light emitting diodes emit light within the 470-550 nm interval.

The sample may be as described above and the irradiation may be carried out as described above.

Figure 1:
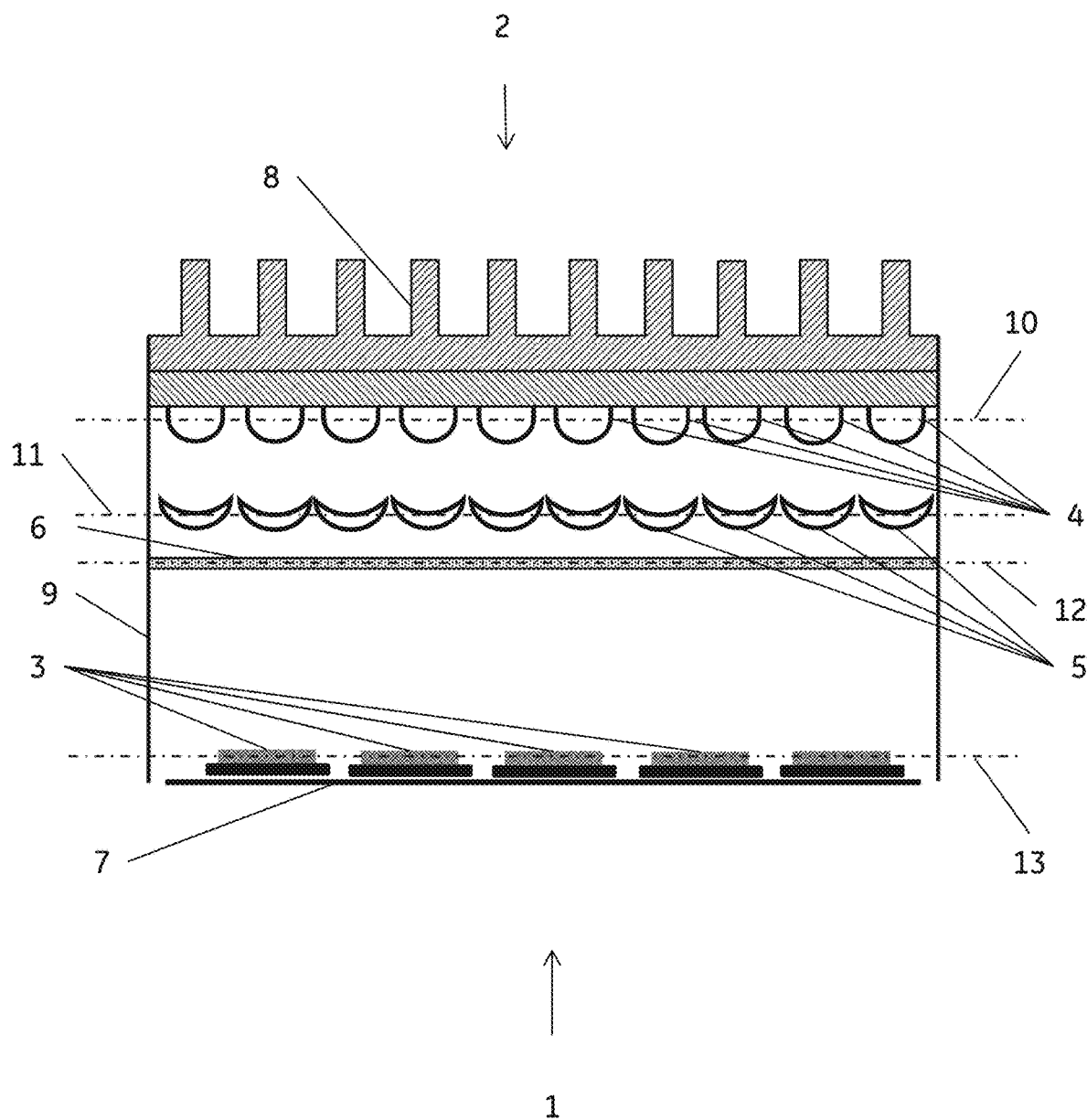
FIG. 1 shows an apparatus of the invention.

In a fourth aspect, illustrated by FIG. 1, the invention discloses an apparatus 1 for reduction of autofluorescence in biological samples 3, comprising a light box 2 with a plurality of LEDs 4, and a plurality of beam spreader lenses 5 and a diffuser plate 6 located between the LEDs and the samples. The plurality of LEDs can be arranged as an array in a plane 10, the plurality of beam spreader lenses can be arranged as an array in a plane 11 and the diffuser plate can be planar and located in a plane 12, with planes 10, 11 and 12 suitable being essentially parallel and with plane 11 located between planes 10 and 12. The plurality of beam spreader lenses and the plurality of LEDs can be arranged so that the light beam from each LED is spread by a beam spreader lens located in front of the LED. The beam spreader lenses can suitably be divergent (negative) lenses, e.g. with focal lengths of about 25 mm. They can e.g. be concave, plano-concave, concavo-convex or Fresnel lenses. The diffuser plate can be a translucent (light-scattering) plate capable of diffusing the light from the LEDs. As an example it can be a ground-glass or etched glass plate. If the focal lengths of the beam spreader lenses is about 25 mm, the distance between plane 10 and plane 11 can be about 2 cm and the distance between plane 11 and plane 12 about 1 cm. The light box 2 can further comprise electrical connections to the LEDs (not shown), a heat sink 8 and side walls 9. The apparatus 1 may optionally further comprise a sample tray 7, for location of one or more biological samples 3, e.g. microscope slide samples. Alternatively, the samples may be located on a desktop below an open-bottom light box or on a bottom wall of the light box. The sample tray and/or the samples may be located in a plane 13, essentially parallel with planes 10, 11 and 12 and with plane 12 between planes 11 and 13. This means that light from the LEDs will be spread by the beam spreader lenses and further spread by the diffuser plate, providing a highly homogeneous illumination of the samples. Optionally, the sample tray may rest on a support or a shaker. The LEDs can suitably emit visible light, e.g. within the wavelength interval of 390-700 nm. In particular, at least 50%, at least 70%, at least 80% or at least 90% of the light intensity from the LEDs may emanate from a wavelength interval with a width of up to 80 nm or up to 70 nm. At least 50%, at least 70%, at least 80% or at least 90% of the light intensity may e.g. emanate from the 470-550 nm interval, such as from the 490-530 nm interval. The total light intensity reaching the samples may e.g. be 5-300 mW/cm², such as 25-300 or 50-200 mW/cm². Suitably, the total light intensity is spatially uniform over the biological samples or the sample tray.

EXAMPLES

The LED light sources used in the examples are listed in Table 2. They were all delivered from ThorLabs Inc, N.J., USA and comprised an LED with a collimator lens. The power data refer to total beam power after passage of the lens. Emission spectra of the LEDs (data from manufacturer) are shown in FIG. 13.

TABLE 2

LED light sources

| LED | Nominal wavelength, nm | Power, mW | Power density, mW/cm² |
|---|---|---|---|
| M385LP1 | 385 | 130 | 165 |
| M455L3 | 455 | 130 | 165 |
| M490L3 | 490 | 60 | 76 |
| M505L3 | 505 | 130 | 165 |
| M530L3 | 530 | 60 | 76 |

Example 1. 505 nm LED Light Treatment

Deparaffinized sections of FFPE CHL (Classical Hodgkin Lymphoma) and T-cell lymphoma tissue samples were mounted on microscope slides and irradiated with 505 nm LED light, using a M505L3 LED, for 30 minutes.

Figure 2:
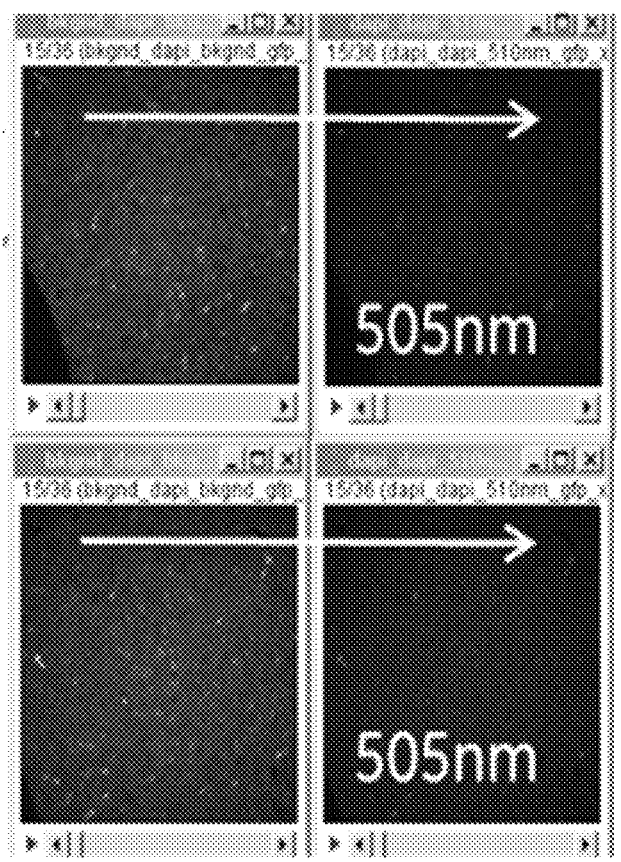
FIG. 2 shows autofluorescence reduction on CHL tissue sections using 505 nm LED light (130 mW/cm$^2$) for 30 minutes.
Figure 3:
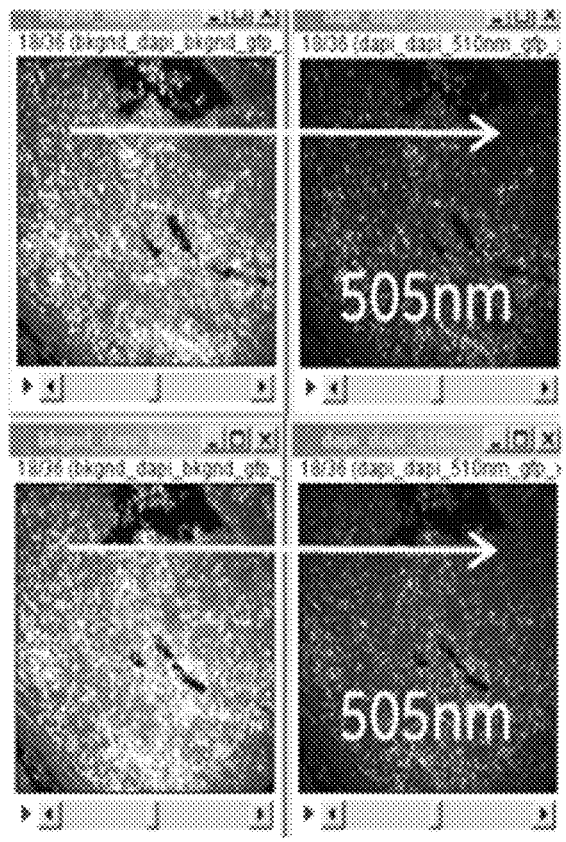
FIG. 3 shows autofluorescence reduction on T-cell tissue sections using 505 nm LED light (130 mW/cm$^2$) for 30 minutes.

The results, as shown in FIG. 2 (CHL) and 3 (T-cell) demonstrate that the light treatment is highly effective in AF reduction.

Example 2. Different LED Wavelengths

Deparaffinized sections of an FFPE Folio T-cell Lymphoma tissue sample were mounted on microscope slides and irradiated for 30 minutes using 5 different LED wavelengths-385, 455, 505, 490 and 530 nm's. The LEDs used were M385LP1, M455L3, M505L3, M490L3 and M530L3.

The results, as shown in FIG. 4, demonstrate that a 30 min irradiation at 490, 505 or 530 nm gives effective AF reduction. LED with wavelengths above 455 nm show AF reduction whereas 385 nm LED exposure shows increase in AF.

Example 3. Different LED Wavelengths

Deparaffinized sections of an FFPE Reactive lymph node tissue sample were mounted on microscope slides and irradiated for 30 minutes using 5 different LED wavelengths-385, 455, 505, 490 and 530 nm's.

The results, as shown in FIG. 5, demonstrate that 30 min irradiation at 490, 505 or 530 nm gives effective AF reduction, whereas 385 and 455 nm LED exposure shows increase in AF.

Example 4. Different LED Wavelengths

Deparaffinized sections of an FFPE Hodgkins lymphoma tissue sample were mounted on microscope slides and irradiated for 30 minutes using 5 different LED wavelengths-385, 455, 505, 490 and 530 nm's.

The results, as shown in FIG. 6, demonstrate that 30 min irradiation at 490, 505 or 530 nm gives effective AF reduction, whereas 385 and 455 nm LED exposure shows increase in AF.

Example 5. Immunofluorescence Staining

Sections from Example 3, which had been subjected to 30 min 505 nm irradiation, were stained with Cy3-labeled anti-CD79 antibodies and with Cy5-labeled anti-PCK26 antibodies. Fluorescence imaging of the stained samples (FIG. 7) show high levels of fluorescence from both markers, demonstrating that the 505 nm exposure did not cause any epitope damage even for a sensitive antigen as CD79.

Example 6. Hypericin, Bilirubin, Hypocrellin and Riboflavin as Triplet Sensitizers Deparaffinized sections of an FFPE Tonsil tissue sample were mounted on microscope slides and contacted with $10^{-9}$M hypericin in PBS buffer, $10^{-6}$M bilirubin in PBS buffer, $10^{-9}$M hypocrellin or $10^{-6}$M riboflavin. The samples were then exposed to visible light (420 nm rayonet bulbs, 5 mW/cm$^2$) for 20 min and the background fluorescence (Cy3-channel) was imaged for each sample and for non-treated background samples (Bkgd). The results (FIG. 8) show that the treatments decreased the background fluorescence.

Example 7. Hypericin+LED Light Treatment

Deparaffinized sections of an FFPE Lung carcinoma tissue sample were mounted on microscope slides and contacted with $1.98*10^{-9}$M hypericin in PBS buffer and exposed for 20 minutes to 226 mW 549 nm LED.

The results in FIG. 9 show that the sensitizer light treatment provides effective AF reduction.

Example 8 Hypericin Concentration Dependence

Deparaffinized sections of an FFPE Lung carcinoma tissue sample were mounted on microscope slides and contacted with $1.98*10^{-6}$M, $1.98*10^{-7}$M, $1.98*10^{-8}$M and $1.98*10^{-9}$M hypericin in PBS buffer and exposed for 20 minutes to 226 mW 549 nm LED.

The results (FIG. 10) indicate that hypericin lower than $10^{-6}$M is most efficient in AF reduction. At higher concentrations sensitizer aggregation or stacking may reduce the sensitization.

Example 9. Immunofluorescence Staining

Deparaffinized sections of an FFPE Diffuse B-Cell Lymphoma tissue sample were mounted on microscope slides and contacted with $10^{-9}$M hypericin in PBS buffer, $10^{-6}$M bilirubin in PBS buffer, $10^{-9}$M hypocrellin or $10^{-6}$M riboflavin. The samples were then exposed to visible light for 20 min and stained with Cy5-labeled anti-NaKATPase antibodies. Fluorescence imaging (FIG. 11) indicates that the NaKATPase antigen has been preserved throughout the treatment.

Example 10. Immunofluorescence Staining

Deparaffinized sections of an FFPE Diffuse B-Cell Lymphoma tissue sample were mounted on microscope slides and contacted with $10^{-9}$M hypericin in PBS buffer, $10^{-6}$M bilirubin in PBS buffer, $10^{-9}$M hypocrellin or $10^{-6}$M riboflavin. The samples were then exposed to visible light for 20 min and stained with Cy3-labeled anti-CD79a antibodies. Fluorescence imaging (FIG. 12) indicates that the CD79a antigen has been preserved throughout the treatment.

Example 11 Light Box

An illumination box for high-throughput AF reduction was constructed according to FIG. 1. This system provides a uniform 505 nm bleaching of a 30 cm×30 cm area (good for a 20-slide sample tray shown). The design is based on a modified high-output industrial backlight panel (MOBL-300×300) with 24 LED's (peak at 505 nm) distributed across the panel's area. The board was custom-modified with addition of a lens array (25 mm focal distance) and a ground-glass diffuser (505-N-P95) to provide sufficient extent of uniformity. The electronic board of the panel is supported by a 24V, 9 Amp DC power adapter, and was optimized for continuous operation by adding an industrial-grade heat sink (otherwise, the panel would have been primarily useful for a strobe-like ignition). Intensity control is accomplished by an in-line variable pot (IVP-C1) connected to the board via an M12 interface (5PM12-J2000 cable).

The LED array combined with the array of lenses and the ground-glass diffuser provides uniform illumination across the 20-sample tray, with the same dose of bleaching for each sample slide. The box represents a low to medium eye safety hazard; hence, operation with a closed lid on the enclosure and side walls is recommended. No special safety eyewear is required; however, prolonged gazing at the tray while the lamp is ON is not recommended.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. Any patents or patent applications mentioned in the text are hereby incorporated by reference in their entireties, as if they were individually incorporated.

What is claimed is:

1. A method for reduction of autofluorescence in biological samples, the method comprising:
   providing one or more biological microscopy samples comprising tissue material;
   contacting the one or more biological microscopy samples with a solution comprising a triplet sensitizer;
   irradiating the one or more biological microscopy samples with visible light having a light intensity, wherein at least 50% of the light intensity emanates from a wavelength interval within the visible range, and wherein the wavelength interval has a width of up to 80 nm,
   wherein the triplet sensitizer combined with the wavelength interval reduces inherent tissue autofluorescence exhibited by the one or more biological microscopy samples compared to that in absence of the triplet sensitizer and in response to a wideband irradiation wavelength interval having a width of greater than 80 nm;
   staining the one or more biological microscopy samples with one or more fluorescent markers; and
   imaging fluorescence from the one or more biological microscopy samples.

2. The method of claim 1, wherein at least 70% of the light intensity emanates from the wavelength interval.

3. The method of claim 1, wherein the wavelength interval has a width of up to 70 nm.

4. The method of claim 1, wherein the light intensity is within a range of 5 mW/cm$^2$ to 300 mW/cm$^2$.

5. The method of claim 1, wherein the one or more biological microscopy samples are irradiated for a time within a range of 5 minutes to 90 minutes.

6. The method of claim 1, wherein the visible light is provided by one or more light emitting diodes (LEDs).

7. The method of claim 1, wherein the light intensity is spatially uniform over the one or more biological microscopy samples.

8. The method of claim 1, wherein the one or more biological microscopy samples are fixed on a microscope slide.

9. The method of claim 1, wherein the one or more biological microscopy samples comprise a section of a formaldehyde fixed paraffin embedded (FFPE) tissue sample.

10. The method of claim 1, further comprising staining the one or more biological microscopy samples with one or more fluorescent markers and imaging fluorescence from the one or more biological microscopy samples.

11. The method of claim 10, wherein the one or more fluorescent markers comprise a fluorescent histological stain, a fluorophore conjugated to an antibody, a fluorophore conjugated to a nucleic acid, and/or a fluorophore conjugated to a lipid.

12. The method of claim 1, wherein the visible light is within a range of 390 nm to 700 nm.

13. The method of claim 1, wherein the wavelength interval is 470 nm to 550 nm.

14. The method of claim 1, wherein the wavelength interval is 490 nm to 530 nm.

15. The method of claim 1, wherein the triplet sensitizer is selected from the group consisting of: riboflavin, bilirubin, hypericin, methylene blue, and hypocrellin.

16. The method of claim 1, wherein at least 80% of the light intensity emanates from the wavelength interval.

17. The method of claim 1, wherein at least 90% of the light intensity emanates from the wavelength interval.

18. The method of claim 1, wherein the light intensity is within a range of 50 mW/cm$^2$ to 200 mW/cm$^2$.

19. The method of claim 1, wherein the one or more biological microscopy samples are irradiated for a time within a range of 10 minutes to 60 minutes.

20. The method of claim 1, wherein the one or more biological microscopy samples are irradiated for a time within a range of 10 minutes to 30 minutes.

21. The method of claim 1, wherein the triplet sensitizer is riboflavin.

22. The method of claim 21, wherein the one or more biological microscopy samples comprise a section of a formaldehyde fixed paraffin embedded (FFPE) tissue sample.

23. The method of claim 1, wherein the triplet sensitizer has an absorption spectrum, and wherein the wavelength interval is within the absorption spectrum of the triplet sensitizer.

24. The method of claim 1, wherein the triplet sensitizer has an absorption spectrum, and wherein the wavelength interval matches the absorption spectrum of the triplet sensitizer.

25. A method for reduction of autofluorescence in biological samples, the method comprising:
   providing one or more biological microscopy samples comprising tissue material;
   contacting the one or more biological microscopy samples with a solution comprising a triplet sensitizer;
   irradiating the one or more biological microscopy samples with visible light or near infrared (NIR) light,
   wherein the triplet sensitizer reduces inherent tissue autofluorescence exhibited by the one or more biological microscopy samples compared to that in the absence of the triplet sensitizer;
   staining the one or more biological microscopy samples with one or more fluorescent markers; and
   imaging fluorescence from the one or more biological microscopy samples.

26. The method of claim 25, wherein the triplet sensitizer is a conjugated aromatic ketone or imide.

27. The method of claim 25, wherein the triplet sensitizer is capable of absorbing the visible light or the NIR light.

28. The method of claim 25, wherein the triplet sensitizer is selected from the group consisting of: riboflavin, bilirubin, hypericin, methylene blue, hypocrellin A, and hypocrellin B.

29. The method of claim 25, wherein a concentration of the triplet sensitizer in the solution is within a range of $10^{-10}$ M to $10^{-5}$ M.

30. The method of claim 25, wherein the visible light or the NIR light is provided by one or more light emitting diodes (LEDs).

31. The method of claim 25, wherein the visible light or the NIR light-has a total light intensity within a range of 25 mW/cm² to 300 mW/cm².

32. The method of claim 25, wherein the one or more biological microscopy samples are irradiated for a time within a range of 5 minutes to 90 minutes.

33. A method for reduction of autofluorescence in biological samples, the method comprising:
- providing one or more biological microscopy samples comprising tissue material;
- contacting the one or more biological microscopy samples with a solution comprising a triplet sensitizer;
- irradiating the one or more biological microscopy samples with visible light from one or more light emitting diodes (LEDs), wherein the one or more LEDs emit light within a wavelength interval of 470 nm to 550 nm, wherein the triplet sensitizer combined with the wavelength interval reduces inherent tissue autofluorescence exhibited by the one or more biological microscopy samples compared to that in the absence of the triplet sensitizer and in response to a wideband irradiation wavelength interval having a width of greater than 80 nm;
- staining the one or more biological microscopy samples with one or more fluorescent markers; and
- imaging fluorescence from the one or more biological microscopy samples.

* * * * *